(12) United States Patent
Abe

(10) Patent No.: US 6,669,628 B2
(45) Date of Patent: Dec. 30, 2003

(54) ELECTRONIC ENDOSCOPE SYSTEM ENABLING DIFFERENT TYPE OF ELECTRONIC ENDOSCOPE TO BE USED

(75) Inventor: Kazunori Abe, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 10/072,970

(22) Filed: Feb. 12, 2002

(65) Prior Publication Data

US 2002/0120179 A1 Aug. 29, 2002

(30) Foreign Application Priority Data

Feb. 23, 2001 (JP) ........................................ 2001-048243

(51) Int. Cl.[7] ................................................. A61B 1/04
(52) U.S. Cl. ...................... 600/118; 600/180; 362/574; 348/69
(58) Field of Search ................................ 600/178, 180, 600/181, 118; 362/574; 348/68–70, 72

(56) References Cited

U.S. PATENT DOCUMENTS 5,896,166 A * 4/1999 D'Alfonso et al. ........... 348/72
6,413,210 B1 * 7/2002 Enomoto .................... 600/178

FOREIGN PATENT DOCUMENTS

JP 11-298907 * 10/1999 ............ A61B/1/04

* cited by examiner

Primary Examiner—John Mulcahy
(74) Attorney, Agent, or Firm—Snider & Associates; Ronald R. Snider

(57) ABSTRACT

When a new processor is connected to an old electronic endoscope provided with a memory storing B data for image processing specific to the scope, white balance control is carried out by a microcomputer. That is, at the time when power is turned on, this microcomputer determines whether or not image processing data compatible with the new processor is present in the old electronic endoscope. If the compatible data are not present, the microcomputer carries out white balance control based on the image of white board picked up by the user, and additionally writes new C data for image processing at the time of white balance control in a memory of the old electronic endoscope together with data identification information. Thereby, the compatibility with an old type of electronic endoscope is maintained.

1 Claim, 3 Drawing Sheets

ELECTRONIC ENDOSCOPE SYSTEM ENABLING DIFFERENT TYPE OF ELECTRONIC ENDOSCOPE TO BE USED

BACKGROUND OF THE INVENTION

This application claims the priority of Japanese Patent Applications No. 2001-48243 filed on Feb. 23, 2001 which is incorporated herein by reference.

1. Field of the Invention

The present invention relates to an electronic endoscope system. More particularly, the present invention relates to a configuration of an electronic endoscope system used by connecting any type of electronic endoscope corresponding to an application portion etc., an electronic endoscope having different optical characteristics, or the like to a common processor.

2. Description of the Related Art

Conventionally, various types of electronic endoscopes have been manufactured to be applied to different portions of human body etc. These electronic endoscopes have a configuration such as to be connected detachably to a processor, and an observed object can be displayed on a monitor by means of an image signal generated from this processor. Specifically, an objective optical system and a CCD (Charge Coupled Device), which are an objective optical system and a solid-state image sensor, are provided in the distal end portion of the electronic scope. By driving this CCD, signals in color pixel units of, for example, cyan (Cy), magenta (Mg), green (G), and yellow (Y) are obtained, and these signals are subjected to image processing such as signal amplification, conversion into color-difference signal and luminance signal or color signal of R (red), G (green), and B (blue), and gamma control with a signal processing circuit of an electronic endoscope and a processor.

In the image processing of the above-mentioned conventional electronic scope, image processing data considering the image pickup conditions specific to the individual electronic scope are stored, and the above-mentioned various processing is performed based on these data. For example, the image processing data include an amplification factor or correction factor for the above-mentioned color signal of Cy, Mg, G and Y, luminance signal, color-difference signal, color signal of R, G and B, etc., a correction factor for gamma correction, or the like. These image processing data are stored in a memory on the electronic scope side and a memory on the processor side, and necessary factor data etc. are read in a predetermined circuit, by which signal processing is performed.

Specifically, since the optical characteristics of the objective optical system and CCD disposed in the distal end portion of the electronic scope differ depending on the type of electronic scope, and also somewhat differ according to the manufacture, the image processing data specific to the electronic scope are stored in the memory on the electronic scope side, and thereby an image with high color reproducibility is formed by the data on the electronic scope side and the data on the processor side.

However, since the image signal processing using the above-mentioned electronic endoscope system is performed by both of the electronic scope and the processor, the processing can be performed only by a plurality of predetermined electronic endoscopes and a processor designed to correspond to these electronic endoscopes. If a new type or different type of electronic endoscope system is developed and manufactured and the signal processing conditions (image processing data) on the processor side are changed, the white balance is lost. Therefore, there arises a problem in that an old type of electronic scope cannot be connected to a new type or different type of processor, so that the electronic scope cannot be used effectively.

SUMMARY OF THE INVENTION

The present invention has been made to solve the above problem, and accordingly an object thereof is to provide an electronic endoscope system in which the compatibility with an old type of electronic endoscope can be maintained even when a new type or a different type of system is manufactured.

To achieve the above object, the present invention provides an electronic endoscope system comprising any type of electronic endoscope having a memory for storing data specific to the scope for image processing for a signal obtained using an image pick-up device; and a processor configured to be connectable with the electronic endoscope, wherein the processor is provided with a signal processing circuit for receiving an image signal from the electronic endoscope for further image processing and a white balance control circuit for carrying out white balance control based on the picked-up image of a white object to control new image processing data based on this control to be written in a memory of the electronic endoscope.

Also, in the present invention, the white balance control circuit of the processor determines whether or not image processing data compatible with the processor are present by referring to data in the memory of the electronic endoscope, and if the compatible image processing data are not present, the white balance control circuit can carry out the white balance control and writing control.

According to the above-described configuration, the white balance control circuit determines whether or not image processing data compatible with the processor are present in the connected electronic endoscope, for example, at the time when power is turned on. If the compatible data are not present, this fact is displayed to prompt the user etc. to carry out white balance control.

Next, the user etc. select white balance control from a menu screen etc., and pick up the image of a white board. Then, the white balance control is carried out by the control circuit, and the image of observed object is displayed under the condition that the control has been carried out. Based on, for example, the user's operation for determining writing, new image processing data at the time of white balance control is additionally written in the memory of the electronic endoscope. Subsequently, signal processing is performed based on the new data.

Further, in the present invention, in the case where an electronic endoscope using a light source as the standard, the light source being different from a light source used in the processor as the standard, is connected to the processor, light source correction data for compensating the difference between the light sources are preferably written in the memory together with the image processing data.

DETAILED DESCRIPTION OF THE PREFERRED EMBODIMENTS

Figure 1:
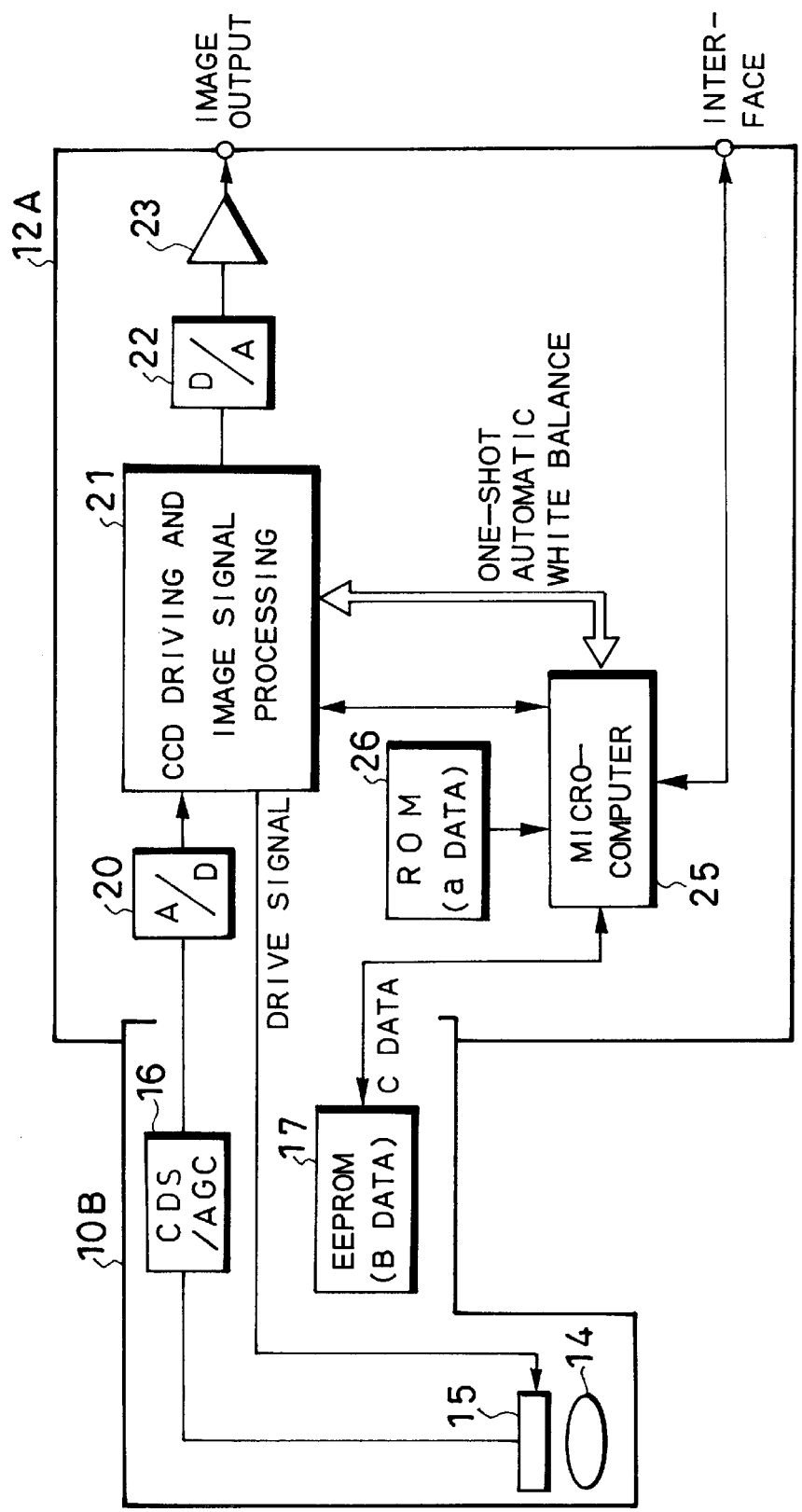
FIG. 1 is a block diagram showing a circuit configuration of an electronic endoscope system in accordance with an embodiment of the present invention, showing a case where an old electronic scope is connected to a new processor.
Figure 2:
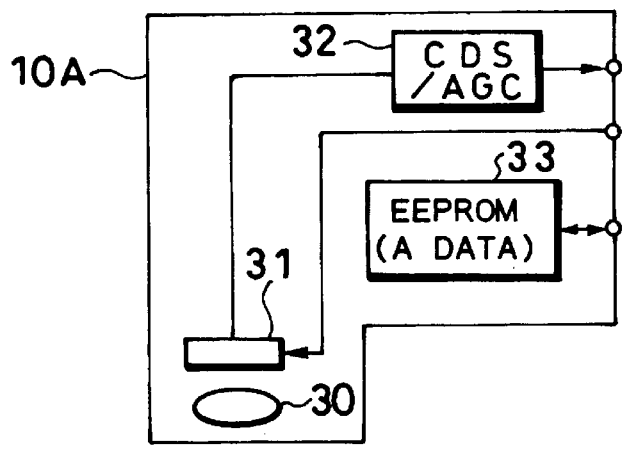
FIG. 2 is a block diagram showing a configuration of a new electronic scope in accordance with an embodiment.

FIGS. 1 to 3 show a configuration of an electronic endoscope system in accordance with the present invention. FIG. 1 shows an internal configuration in a state in which an old type of electronic endoscope 10B is connected to a new type of processor 12A, and FIG. 2 shows an internal configuration of a new type of electronic endoscope 10A. Referring to FIG. 1, the old electronic endoscope 10B is provided with a CCD 15 via an objective optical system 14 in the distal end portion thereof. Also, in the old electronic endoscope 10B, a CDS/AGC circuit 16 or the like for subjecting an output signal from the CCD 15 to correlated double sampling (CDS) and automatic gain control (AGC) is provided.

The old electronic endoscope 10B is provided with a writable or reprogrammable memory (EEPROM etc.) 17 for storing image processing data (hereinafter referred to B data) and the like. The B data stored in this memory include an amplification factor or correction factor for a color signal of Cy, Mg, G and Y, luminance signal, color-difference signal, color signal of R, G and B, etc., a correction factor for gamma correction, or the like.

Figure 3A:
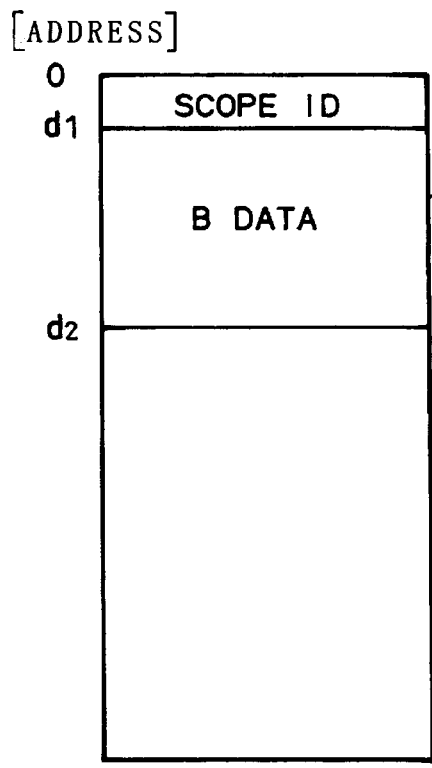
FIG. 3A is a diagram showing data in a memory at the time of manufacture provided in the old electronic scope shown in FIG. 1.
Figure 3B:
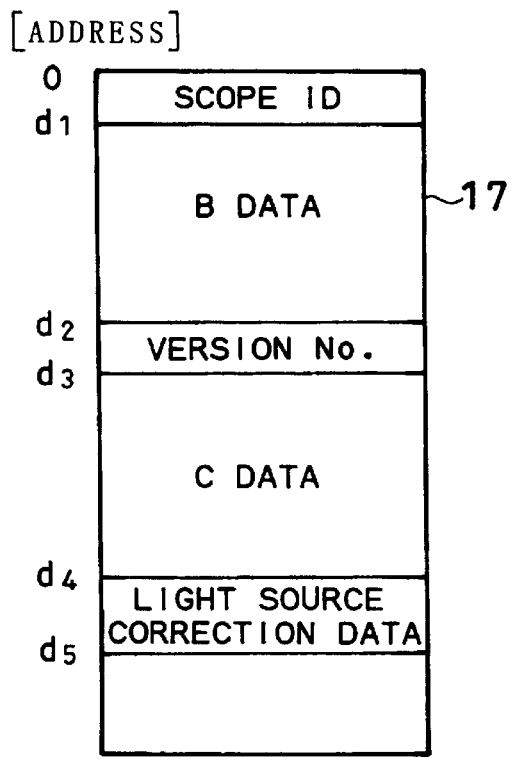
FIG. 3B is a diagram showing a state in which new data are input by white balance control in the old electronic scope shown in FIG. 1.

FIGS. 3A and 3B show data in the above-mentioned memory 17. At the stage at which the old electronic endoscope 10B is manufactured, as shown in FIG. 3A, scope ID data stored at address 0 to $d_1$ and the above-mentioned B data for image processing written at address $d_1$ to $d_2$ are stored in the memory 17.

On the other hand, the new processor 12A shown in FIG. 1 is provided with an A/D converter 20 for receiving an output signal from the CDS/AGC circuit 16, a CCD driving and image signal processing circuit 21 for sending a drive signal to the CCD 15 and performing conversion processing for forming a luminance signal and color-difference signal from the output of the A/D converter 20, or processing for converting into a color signal of R, G and B, etc., gamma correction, contour enhancement, and other various processing, a D/A converter 22, and an output amplifier 23. The configuration is not limited to the above-described one. For example, a part of the CCD driving and image signal processing circuit 21, for example, a CCD drive signal generating circuit may be disposed in the old electronic endoscope 10B, or the CDS/AGC circuit 16 may be disposed in the new processor 12A.

In the new processor 12A, a microcomputer 25 for collectively controlling various processing and carrying out white balance control (one-shot automatic white balance control) and a memory (ROM) 26 for storing processor data for image processing (hereinafter referred to a data) are provided. Specifically, the microcomputer 25 reads the data in the memory (17) of the scope connected, and determines whether or not data compatible with the new processor (later-described C data or A data of the new electronic endoscope) are present. If the compatible data is not present, the white balance control is carried out and new image processing data (hereinafter referred to as C data) in the electronic endoscope are prepared based on this control by a selective operation of the user, and the C data are additionally written (or rewritten) in the memory in the electronic endoscope together with the identification information (version No. etc.) for the image processing data.

FIG. 2 shows a configuration of a new electronic endoscope 10A manufactured together with the new processor 12A. The new electronic endoscope 10A is similarly provided with an objective optical system 30, a CCD 31, and a CDS (correlated double sampling)/AGC (automatic gain control) circuit 32. The new electronic endoscope 10A is also provided with a writable or reprogrammable memory (EEPROM etc.) 33 for storing image processing data (referred to as A data (standard data)). The use of the A data together with a data provides an image having high color reproducibility in the new processor 12A without carrying out the above-mentioned white balance control.

Figure 4:
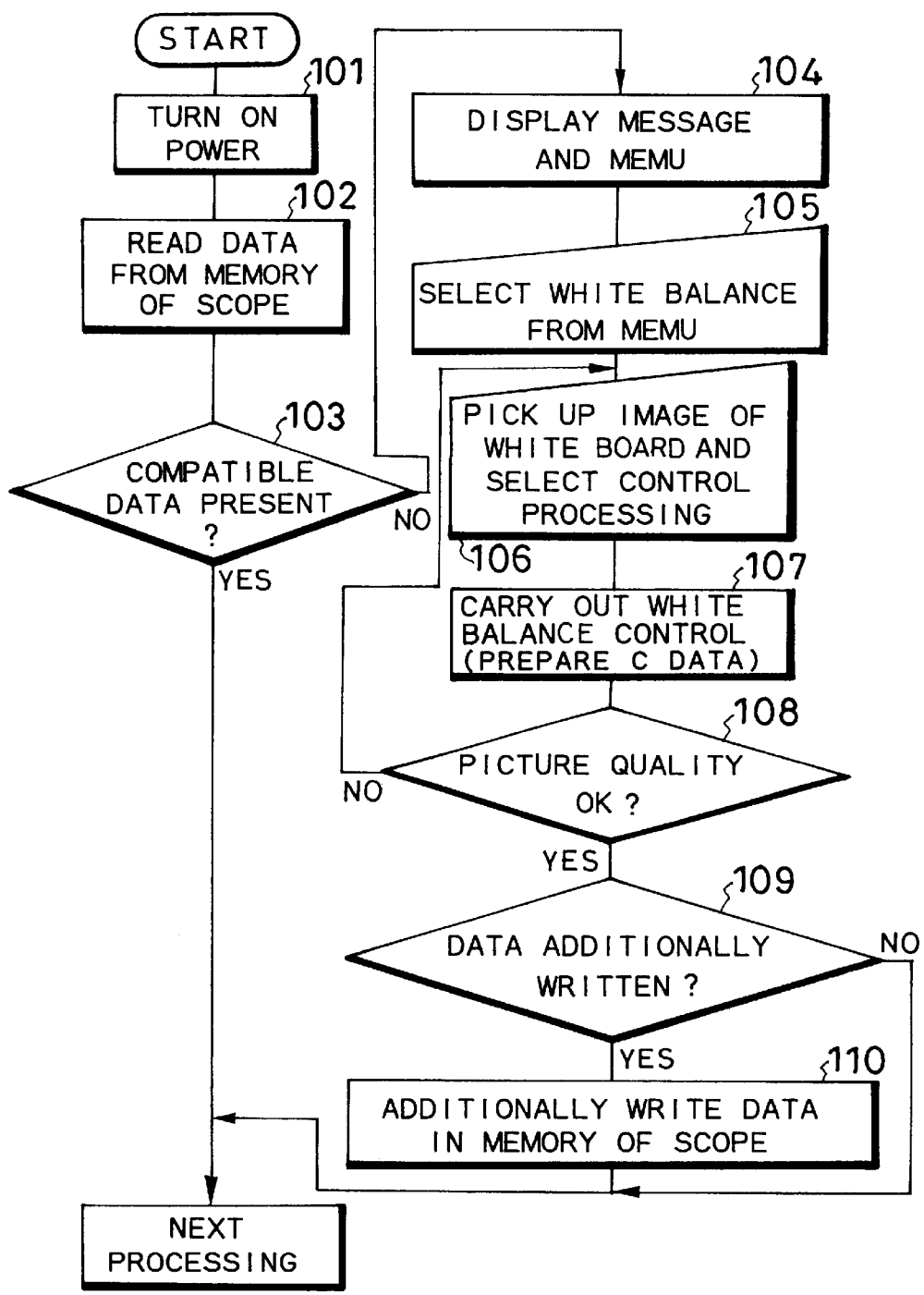
FIG. 4 is a flowchart showing a principal operation of an embodiment.

The operation of the embodiment having the above-described configuration will be described with reference to FIG. 4. After the old electronic endoscope 10B has been connected to the new processor 12A as shown in FIG. 1, the power for the processor 12A is turned on. Then, in step 102, the microcomputer 25 communicates with the old electronic endoscope 10B and thus reads data in the memory 17. In the next step 103, a determination is made as to whether or not compatible data for image processing are present. This determination is made based on old or new of scope determined by the scope ID data at address 0 to $d_1$ and the version No. at address $d_2$ to $d_3$. Specifically, since the old electronic endoscope 10B shown in FIG. 1 is in a state in which the version No. is not present as shown in FIG. 3A, it is determined that C data or A data, which are compatible data, are not present.

If it is determined that the compatible data are not present (NO) in step 103, the control goes to step 104, where a message and a menu are displayed. For example, a message of "No compatible data" and a menu screen for selecting either of the image pickup using the standard data and the one-shot white balance (control processing) are displayed on a monitor. In the next step 105, the one-shot white balance is selected from the menu screen. In step 106, after the image of a white board has been picked up, for example, if the control processing is selected on a screen displayed next, the white balance control is carried out in step 107. Specifically, the microcomputer 25 automatically performs control processing for changing the B data so that the white color of white board is displayed exactly, and retains the correction data (C data) at this time (stores the data in not-illustrated RAM etc.).

Next, in step 108, a screen for determining, for example, whether or not the picture quality of monitor is OK'd is displayed to ask whether or not the present control state is OK'd. If the user selects OK, for example, by picking up the image of an appropriate object, in step 109, the user is asked whether or not the control data is additionally written by the similar selection display (whether or not the control state is determined). If YES is selected in both steps 108 and 109, the control proceeds to step 110, where C data (address $d_3$ to $d_4$) are additionally written together with version No. (address $d_2$ to $d_3$) at a place separate from B data in the memory 17 of the old electronic endoscope 10B as shown in FIG. 3B. The C data are a substitute for B data.

Further, in the above-mentioned step 103, if it is determined that the compatible data are present, image processing is performed after passing through the next processing without the selection of one-shot white balance. For example, when the old electronic endoscope 10B in which new C data have been additionally written as described above is used again, the presence of C data is verified by the determination of the version No., and image processing is accomplished based on the C data. As a result, an image having good white balance and high color reproducibility can be obtained.

In the above-mentioned new processor 12A, a lamp that is different from a light source lamp disposed in an old processor corresponding to the old electronic endoscope 10B is sometimes used. For example, in the case where a halogen lamp is used in the old processor, while a xenon lamp is used in the new processor, light source correction data for compensating the difference in lamp are additionally written at address $d_4$ to $d_5$ as shown in FIG. 3B at the time of the above-mentioned white balance control. Thereby, even when a different lamp is used, high color reproducibility can be achieved.

Also, in the case where the new electronic endoscope 10A shown in FIG. 2 is connected to the new processor 12A, it is determined, by the determination of scope ID, that standard A data compatible with the processor 12A is present, and image processing is performed based on the A data, so that an image having high color reproducibility is obtained.

In the above-described embodiment, since new C data is additionally written in the memory of the old electronic endoscope 10B with B data being left, it is natural for the old electronic endoscope 10B to be capable of being used by being connected to the old processor. However, if the old processor is not used at all, B data may be erased and C data may be rewritten together with version No.

As described above, according to the present invention, even when a new type or different type of electronic endoscope system is manufactured, the compatibility with an old type of electronic endoscope is maintained, and thus an image having high color reproducibility can always be obtained.

What is claimed is:

1. An electronic endoscope system comprising:

any type of electronic endoscope having a memory for storing data specific to the scope for image processing for a signal obtained using an image pick-up device;

a processor configured to be connectable with said electronic endoscope, wherein said processor is provided with a signal processing circuit for receiving an image signal from said electronic endoscope for further image processing and a white balance control circuit determines whether or not image processing data compatible with said processor are present by referring to data in the memory of said electronic endoscope, and if the compatible image processing data are not present, said white balance control circuit carries out white balance control based on the picked-up image of a white object, and additionally write new image processing data based on this control in a memory of said electronic endoscope with old data being left, and wherein in the case where an electronic endoscope using a light source as the standard, said light source being different from a light source used in said processor as the standard, is connected to the processor, light source correction data for compensating the difference between the light sources are independently written in the memory of said electronic endoscope.

* * * * *